US012714496B2

(12) United States Patent
Fuentes Castro et al.

(10) Patent No.: US 12,714,496 B2
(45) Date of Patent: Aug. 25, 2026

(54) MEDICAL DEVICES AND RELATED METHODS FOR DELIVERING ENERGY AND/OR FLUID

(71) Applicants: Boston Scientific Scimed, Inc., Maple Grove, MN (US); Boston Scientific Medical Device Limited, Galway (IE)

(72) Inventors: Julian Fuentes Castro, La Unión (CR); Juan Pablo Ortiz Garcia, Heredia (CR); Kensuke Hayashi, Newton, MA (US); Takashi Toyonaga, Kobe (JP)

(73) Assignees: Boston Scientific Scimed, Inc., Maple Grove, MN (US); Boston Scientific Medical Device Limited, Galway (IE)

( * ) Notice: Subject to any disclaimer, the term of this patent is extended or adjusted under 35 U.S.C. 154(b) by 201 days.

(21) Appl. No.: 18/623,589

(22) Filed: Apr. 1, 2024

(65) Prior Publication Data

US 2024/0335227 A1 Oct. 10, 2024

Related U.S. Application Data

(60) Provisional application No. 63/494,532, filed on Apr. 6, 2023.

(51) Int. Cl.
*A61B 18/12* (2006.01)
*A61B 18/14* (2006.01)
(Continued)

(52) U.S. Cl.
CPC .................... *A61B 18/1492* (2013.01); *A61B 2018/00178* (2013.01); *A61B 2018/00267* (2013.01);
(Continued)

(58) Field of Classification Search
CPC ............ A61B 18/1485; A61B 18/1492; A61B 2018/00178; A61B 2018/00196;
(Continued)

(56) References Cited

U.S. PATENT DOCUMENTS 5,782,840 A * 7/1998 Nakao .................... A61B 18/14 606/113
6,093,185 A * 7/2000 Ellis .................. A61B 18/1492 607/101
(Continued)

FOREIGN PATENT DOCUMENTS

CN 210056209 U 2/2020
CN 111671514 A 9/2020
(Continued)

OTHER PUBLICATIONS

International Search Report and Written Opinion for PCT/US2024/022486 dated Jul. 12, 2024 (11 pages).

*Primary Examiner* — Daniel W Fowler
(74) *Attorney, Agent, or Firm* — Bookoff McAndrews, PLLC

(57) ABSTRACT

A medical device for delivering energy and/or fluid includes a handle, a shaft extending distally from the handle, a fluid port configured to deliver fluid through at least a portion of the shaft, and an end effector at a distal end of the shaft. The handle includes a hub for electrically connecting the medical device to an energy source. The shaft includes an outer sheath, an inner sheath, and a control wire. The end effector includes a loop portion and an electrode coupled to a distal end of the loop portion. A proximal end of the loop portion is coupled to a distal end of the control wire such that movement of the control wire controls a position of the end effector relative to the distal end of the shaft.

20 Claims, 8 Drawing Sheets

(51) Int. Cl.
*A61B 18/00* (2006.01)
*A61M 25/00* (2006.01)

(52) U.S. Cl.
CPC ............... *A61B 2018/00601* (2013.01); *A61B 2018/0091* (2013.01); *A61B 2018/1407* (2013.01); *A61B 2018/141* (2013.01); *A61B 2018/1475* (2013.01); *A61B 2218/002* (2013.01); *A61M 25/0097* (2013.01)

(58) Field of Classification Search
CPC ........... A61B 2018/00267; A61B 2018/00482; A61B 2018/00559; A61B 2018/00601; A61B 2018/0091; A61B 2018/1407; A61B 2018/141; A61B 2018/1475
See application file for complete search history.

(56) References Cited

U.S. PATENT DOCUMENTS

2005/0159648 A1* 7/2005 Freed .............. A61B 17/32056 600/113
2006/0050143 A1* 3/2006 Ouchi ................ A61B 18/1492 348/65
2013/0041373 A1* 2/2013 Laufer .................. A61B 18/14 606/47
2016/0008063 A1* 1/2016 Wake ................ A61B 17/3203 606/49
2016/0095649 A1* 4/2016 Motai .................... A61B 17/42 606/46
2017/0105797 A1* 4/2017 Mikkaichi .............. A61B 18/14
2020/0315437 A1* 10/2020 Yuasa .................... A61B 1/018
2020/0352643 A1 11/2020 Jensrud et al.
2022/0273363 A1 9/2022 Scott et al.
2023/0190321 A1* 6/2023 Jung .................. A61B 18/1482 606/205
2023/0277237 A1* 9/2023 Kou ................... A61B 18/1206 606/41

FOREIGN PATENT DOCUMENTS

CN 115137474 A 10/2022
WO 2023033200 A1 3/2023

* cited by examiner

FIG. 2C
104
158
156
126
114C
114B
114A
128D
128B
128
114
128A
158
112
130
152
116
106
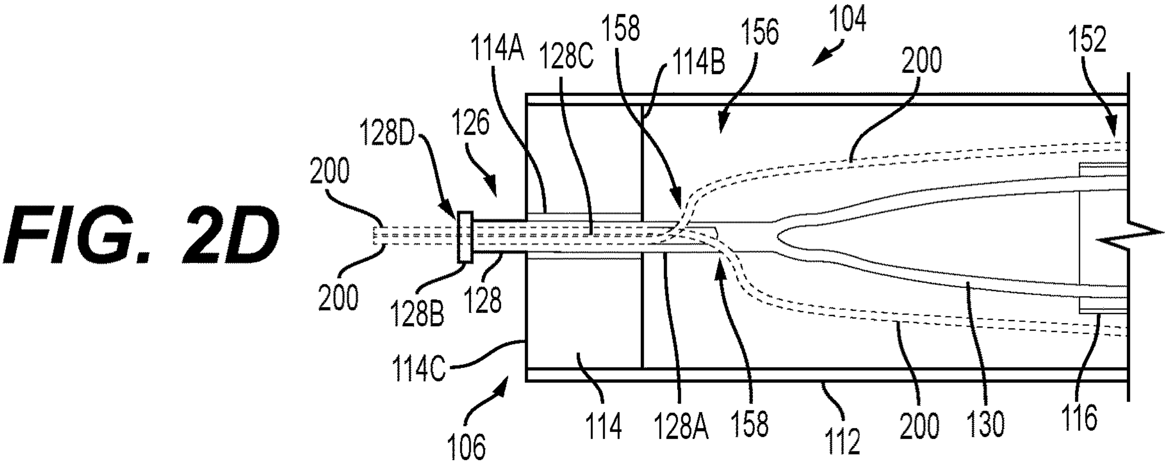
FIG. 2D
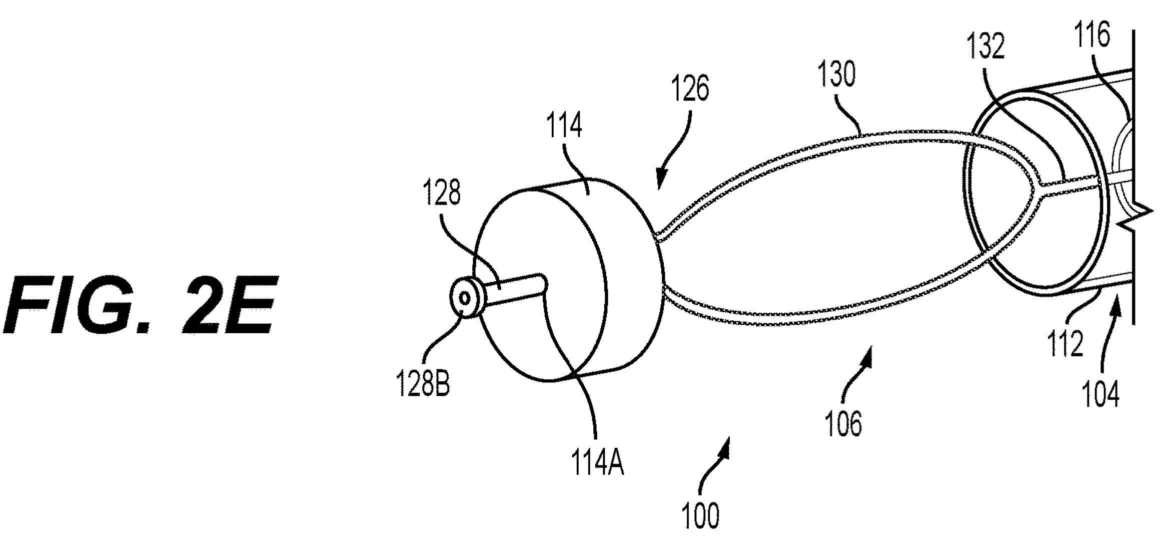
FIG. 2E

228E
A
264
258
258
228A
268

228C
266
228
228B
A
228D
228E
A
264
258
258
268
228A 228C
266
228
228B
A
228D 312B
332
312
316B
316

300
326
328B
328
330
312A
D
306
P
316
304
312

312A
312B
316A
316B
328B
D
306
328
326
316
312
300
330
P
304

428
428B
D
426
470
470
472
430
432
P
416

528B
528
526
D
580
580
530
580
580
532
P
516

MEDICAL DEVICES AND RELATED METHODS FOR DELIVERING ENERGY AND/OR FLUID

CROSS-REFERENCE TO RELATED APPLICATIONS

This application claims priority to U.S. Provisional Application No. 63/494,532, filed on Apr. 6, 2023, which is incorporated by reference herein in its entirety.

TECHNICAL FIELD

Aspects of this disclosure generally relate to medical devices and related methods for delivering energy and/or fluid. Embodiments of the disclosure relate to medical devices and related methods of treating tissue by delivering electrical energy to or into tissue and/or injecting fluid into, under, and/or around tissue with a treatment device that includes an electrode and/or a loop.

BACKGROUND

Medical devices, such as endoscopes or other suitable insertion devices, are employed for a variety of types of diagnostic and surgical procedures, such as endoscopy, laparoscopy, arthroscopy, gynoscopy, thoracoscopy, cystoscopy, etc. Many of these procedures involve delivering energy to tissue of an organ or a gland to treat lesions (e.g., tumors), infections, and the like. Examples of such procedures include Endoscopic Mucosal Resection (EMR), Endoscopic Sub-mucosal Resection (ESR), Endoscopic Submucosal Dissection (ESD), polypectomy, mucosectomy, etc. In particular, such procedures may be carried out by inserting an insertion device into a subject's body through a surgical incision, or via a natural anatomical orifice (e.g., mouth, vagina, or rectum), and performing the procedure or operation at a target site with an auxiliary device inserted through the insertion device.

At times, during a medical procedure, a user may use an injection needle, an energy delivery device, and/or a loop or snare for purposes of raising, separating, flushing, cutting, dissecting, ablating, marking, coagulating, cauterizing, or otherwise treating and/or manipulating tissue. The injection, energy delivery, and/or resection may be performed separately. For example, in order to deliver energy to the tissue, the user may be required to remove the injection needle from the insertion device and deliver the energy delivery device through the insertion device to the tissue being targeted, and vice versa. Moreover, in order to resect the tissue, the user may be required to remove the energy delivery device from the insertion device and deliver the loop or snare through the insertion device to the tissue being targeted, and vice versa. During the procedure, the user may alternate using the injection needle, the energy delivery device, and/or the loop or snare, and exchanging devices may increase the duration and risks of the medical procedure.

The devices and methods of this disclosure may rectify one or more of the deficiencies described above or address other aspects of the art.

SUMMARY

Examples of the disclosure relate to, among other things, medical devices configured for treating tissue by electrical energy to the tissue, either via an electrosurgical knife and/or a loop, and methods for using the medical devices. In some examples, the medical devices may also be configured to deliver fluid into, under, and/or around the tissue. Each of the examples disclosed herein may include one or more of the features described in connection with any of the other disclosed examples.

In one example, a medical device for delivering energy and/or fluid may include a handle, a shaft extending distally from the handle, a fluid port configured to deliver fluid through at least a portion of the shaft, and an end effector at a distal end of the shaft. The handle may include a hub for electrically connecting the medical device to an energy source. The shaft may include an outer sheath, an inner sheath, and a control wire. The end effector may include a loop portion and an electrode coupled to a distal end of the loop portion. A proximal end of the loop portion may be coupled to a distal end of the control wire such that movement of the control wire controls a position of the end effector relative to the distal end of the shaft.

The medical device may include one or more of the following features. The medical device may further include an end cap. The end cap may include an opening extending longitudinally through a portion of the end cap. A portion of the electrode may extend through the opening of the end cap. The end cap may be formed of rubber, may be fixedly coupled to a portion of the electrode, and may be movable relative to a distal end of the outer sheath. The electrode may include an electrode lumen fluidly connected to the fluid port. A distal end of the electrode may include an outlet. A proximal portion of the electrode may include one or more inlets fluidly connected to the electrode lumen. The electrode may include a widened distal end. The electrode may include a proximal longitudinal portion, a distal longitudinal portion, and a tapered portion between the proximal longitudinal portion and the distal longitudinal portion. The tapered portion may be configured to engage with a proximal portion of the end cap to advance the end cap distally. The loop portion may form an opening. The opening may include a wide portion and a tapered or narrowed portion toward a distal end of the loop portion.

The handle may include main body and a movable body. The movable body may be movable within a slot in the main body. The hub may be positioned on a portion of the movable body. The movable body may be coupled to the control wire to deliver energy to the end effector and to movement of the end effector relative to the shaft. The main body may include a plurality of contours. The movable body may include one or more detents that interact with one or more of the plurality of contours to lockably position the movable body relative to the main body. The fluid port may be coupled to one or more of the inner sheath and the outer sheath at a position distal to the handle. The fluid port may be configured to deliver fluid through a cavity between the inner sheath and the outer sheath. The fluid port may be configured to deliver fluid through a lumen within the inner sheath. The end effector may include a netting extending across one or more portions of the loop portion. The loop portion of the end effector may include a plurality of wires forming a basket.

In another aspect, a medical device for delivering energy and/or fluid may include a handle, a shaft extending distally from the handle, a fluid port, and an end effector. The handle may include a hub for electrically connecting the medical device to an energy source. The shaft may include an outer sheath, an inner sheath, and a control wire. The fluid port may be configured to deliver fluid through at least a portion of the shaft. The end effector may be at a distal end of the shaft. The end effector may include a loop portion and an electrode coupled to a distal end of the loop portion. A proximal end of the loop portion may be coupled to a distal end of the control wire such that movement of the control wire controls a position of the end effector relative to the distal end of the shaft.

The medical device may include one or more of the following features. The medical device may further include a cavity between the inner sheath and the outer sheath. The cavity between the inner sheath and the outer sheath may be fluidly connected to the fluid port to deliver fluid through the cavity. The medical device may also include an end cap at a distal end of the outer sheath. The end cap may include an opening that receives a portion of the electrode. The end cap may be formed of rubber, may be fixedly coupled to a portion of the electrode, and may be movable relative to a distal end of the outer sheath. The handle may include a main body and a movable body. The hub may be positioned on a portion of the movable body. The movable body may be coupled to the control wire to deliver energy to the end effector and to control movement of the end effector relative to the shaft. The main body may include a plurality of contours, and the movable body may include one or more detents that interact with one or more of the plurality of contours to lockably position the movable body relative to the main body.

In yet another aspect, a method of treating a treatment site may include delivering a distal end of a shaft of a medical device to the treatment site. The medical device may include a handle, a shaft with a distal end, and an end effector movable relative to the distal end of the shaft. The shaft may include an outer sheath and an inner sheath. The end effector may include an electrode and a loop portion. The handle may include a movable body and a main body, and movement of the movable body may control a position of the end effector. The method may also include delivering energy to the treatment site with the electrode of the end effector, and delivering fluid to the treatment site. Delivering fluid may include delivering fluid through a port coupled to one or more of the inner sheath and the outer sheath to deliver fluid distally through a cavity between the inner sheath and the outer sheath such that the fluid flows distally into a distal cavity within the outer sheath and into an electrode lumen via one or more inlets in a proximal portion of the electrode. The method may also include extending the end effector distally. Extending the end effector distally may include distally advancing the movable body of the handle to urge the end effector distally. The method may also include delivering energy to the treatment site with the loop portion of the end effector.

The method may include one or more of the following features. Delivering energy to the treatment site with the electrode may be configured to cut tissue. Delivering energy to the treatment site with the loop portion may be configured to resect tissue.

It may be understood that both the foregoing general description and the following detailed description are exemplary and explanatory only and are not restrictive of the disclosure, as claimed.

BRIEF DESCRIPTION OF THE DRAWINGS

The accompanying drawings, which are incorporated in and constitute a part of this specification, illustrate exemplary aspects of the disclosure and together with the description, serve to explain the principles of the disclosure.

FIGS. 2A-2E illustrate various views of portions of the medical device of FIGS. 1A and 1B, including a multifunctional end effector, according to aspects of this disclosure.

DETAILED DESCRIPTION

Examples of the disclosure include devices and methods for one or more of: facilitating and improving the efficacy, efficiency, and safety of treating and/or manipulating tissue when, for example, applying electrical energy to tissue with an electrode; delivering fluid into, under, and/or around tissue during a medical procedure through the distal end of the electrode; and cutting, resecting capturing, or otherwise treating tissue. Aspects of the disclosure may provide the user with the ability to apply electrical energy or heat to tissue using a medical device having an electrode, and to deliver fluid into and/or under tissue with the same medical device. Aspects of the disclosure may provide the user with the ability to apply electrical energy or heat and also deliver fluid without having to switch or swap out end effectors. Aspects of the disclosure may help the user penetrate a layer of tissue (e.g., a submucosal layer) to cause perforation or otherwise cut, cauterize, capture, or otherwise treat tissue. Aspects of the disclosure may help the user cut, resect, capture, or otherwise remove tissue or other material without having to switch or swap out end effectors. Some aspects of the disclosure may be used in performing an endoscopic, laparoscopic, arthroscopic, gynoscopic, thoracoscopic, cystoscopic, or other type of procedure.

Reference will now be made in detail to examples of the disclosure described above and illustrated in the accompanying drawings. Wherever possible, the same reference numbers will be used throughout the drawings to refer to the same or like parts.

The terms "proximal" and "distal" are used herein to refer to the relative positions of the components of an exemplary medical device. When used herein, "proximal" refers to a position relatively closer to the exterior of the body of a subject or closer to a user, such as a medical professional, holding or otherwise using the medical device. In contrast, "distal" refers to a position relatively further away from the medical professional or other user holding or otherwise using the medical device, or closer to the interior of the subject's body. Proximal and distal directions are labeled with arrows marked "P" and "D", respectively, throughout various figures. As used herein, the terms "comprises," "comprising," "having," "including," or other variations thereof, are intended to cover a non-exclusive inclusion, such that a device or method that comprises a list of elements does not include only those elements, but may include other elements not expressly listed or inherent thereto. Unless stated otherwise, the term "exemplary" is used in the sense of "example" rather than "ideal." As used herein, the terms "about," "substantially," and "approximately," indicate a range of values within +/−10% of a stated value.

Figures 1A, 1B:
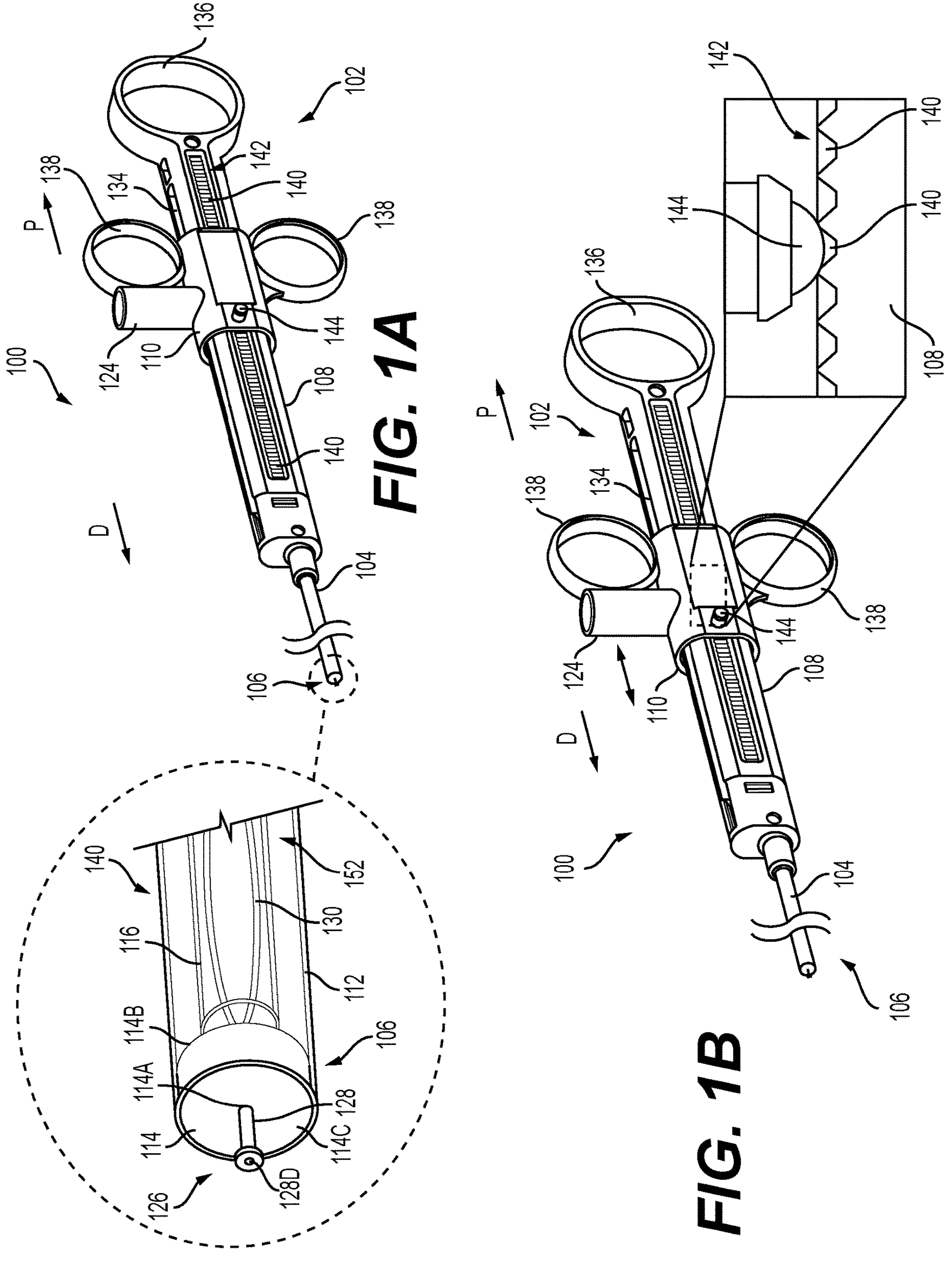
FIGS. 1A and 1B illustrate an exemplary medical device, with FIG. 1A including an enlarged view of a distal portion of the medical device and FIG. 1B including an enlarged cross-sectional view of a proximal portion of the medical device, according to aspects of this disclosure.

FIGS. 1A and 1B depict a medical device 100 that includes a handle 102, a shaft 104, and a distal end 106. Handle 102 may include a main body 108 and a movable body 110. Handle 102 also may include or otherwise be coupled to or adjacent to a port 122 (FIG. 2A) configured to receive fluid. Handle 102 may also include or otherwise be coupled to a hub 124 configured to receive electrical energy similar to an electrical plug or socket. Distal end 106 includes an end effector, for example, a multifunctional end effector 126. As discussed in detail below, end effector 126 may include an energy delivery portion or an electrode portion 128 (hereinafter "electrode 128") and a loop portion 130 (e.g., forming a snare). Both electrode 128 and loop portion 130 are conductive to convey and deliver energy to tissue or other material at a treatment site. The position of movable body 110 relative to main body 108 controls the position of end effector 126 relative to shaft 104. Furthermore, the position of end effector 126 relative to shaft 104 affects whether electrode 128 only or electrode 128 and loop portion 130 is/are extended distally of shaft 104. The position of end effector 126 may also control the delivery of a fluid (e.g., through a portion of electrode 128). In some aspects, shaft 104, including distal end 106, may be delivered to the treatment site via an insertion device (not shown), such as, for example, a scope (e.g., endoscope, duodenoscope, colonoscope, or other type of scope).

Furthermore, a proximal portion of electrode 128 may be coupled to a distal portion of loop portion 130 (e.g., as shown in FIGS. 2C, 2D, 3A, and 3B). End effector 126 is electrically connected to hub 124, and as discussed in detail below, may include one or more channels fluidly connected to, or otherwise in fluid communication with, port 122. A proximal portion of loop portion 130 may be coupled to a control wire 132 (FIG. 3B), for example, coupling end effector 126 to hub 124 (e.g., on movable body 110 of handle 102). In these aspects, end effector 126 (e.g., electrode 128 and loop portion 130) are conductive. Additionally, although not shown, one or more portions of end effector 126 (e.g., a distal portion of electrode 128) may include insulation, for example, radially surrounding one or more portions of end effector 126.

As shown in the inset of FIG. 1A, shaft 104 includes a sheath, for example, an outer sheath 112. Outer sheath 112 may be at least partially insulating. Moreover, distal end 106 includes an end cap 114. End cap 114 may be coupled (e.g., releasably or fixedly coupled) to outer sheath 112 via welding, an adhesive, crimping, friction fit, or other appropriate coupling. End cap 114 may be at least partially insulating, and may at least partially flexible. For example, end cap 114 includes an opening 114A. As shown in FIGS. 2C and 2D, opening 114A may extend longitudinally though a portion of end cap 114, for example, through a radial center of end cap 114. End cap 114 includes a proximal face 114B and a distal face 114C, and opening 114A may extend through end cap 114 from proximal face 114B to distal face 114C. In these aspects, at least a portion of end effector 126 may be extend through opening 114A. Moreover, in some aspects, at least a portion of end effector 126 may be movable (e.g., distally extendable and proximally retractable) relative to end cap 114 through opening 114A, for example, as controlled by a position of movable body 110 relative to main body 108. Additionally, at least a portion (e.g., proximal face 114B) of end cap 114 may be received within and/or otherwise coupled to a distal portion of outer sheath 112, for example, to form a seal at distal end 106. In some aspects, end cap 114 may include a tapered shape, for example, such that proximal face 114B is smaller (e.g., has a smaller cross-sectional area) than distal face 114C. The tapered shape of end cap 114 may help to allow for a portion of end cap 114 to be inserted (e.g., reinserted) into outer sheath 112.

Shaft 104 may also include an internal sheath, for example, an inner sheath 116. Outer sheath 112 and/or inner sheath 116 may be formed of a biocompatible polymer material (e.g., including one or more layers of polymer material), for example, a plastic material. It is noted that FIG. 1A illustrates outer sheath 112 and inner sheath 116 as being transparent, in order to show the respective internal components. However, it is noted that one or more of outer sheath 112 and/or inner sheath 116 may be opaque or otherwise not transparent. Moreover, the distal end of inner sheath 116 may be proximal of end cap 114. Alternatively, although not shown, inner sheath 116 may be temporarily coupled to or otherwise extend to a proximal end of face of end cap 114. In some aspects, a distal end of inner sheath 116 may abut or be positioned adjacent to proximal face 114B of end cap 114 when end cap 114 is retracted at least partially within outer sheath 112. Furthermore, end cap 114 is movable relative to inner sheath 114.

Additionally, as discussed below, one or more of outer sheath 112 and/or inner sheath 116 may be fluidly coupled to a fluid port (e.g., port 122 in FIG. 2A) to deliver fluid through shaft 104 (e.g., through one or more of outer sheath 112 and/or inner sheath 116) and to a treatment site adjacent to distal end 106. For example, end effector 126 may include one or more fluid lumens 128C (FIGS. 2D, 3C, and 3D) and at least one outlet 128D (e.g., in a distal end of electrode 128). Inner sheath 116 may help to direct fluid into a portion of end effector 126, such that fluid is delivered to the treatment site via outlet 128D. Additionally, the coupling of end cap 114 with outer sheath 112, along with at least some flexibility of end cap 114, may help to form a seal, such that fluid is only delivered to the treatment site via outlet 128D, and not through opening 114A or other portions of distal end 106, when fluid travels through, e.g., outer sheath 112.

In some aspects, one or more portions of end effector 126 may be positioned within inner sheath 116. For example, end effector 126 (e.g., including one or more portions of electrode 128 and loop portion 130) may be positioned radially within inner sheath 116 in at least some configurations of end effector 126. End effector 126 may be longitudinally movable relative to inner sheath 116. As mentioned, movement or position of movable body 110 (e.g., relative to main body 108 of handle 102) may control the movement or position of end effector 126 relative to distal end 106. In some aspects, the position of movable body 110 controls whether a portion of electrode 128 extends distally of outer sheath 112 (FIGS. 1A, 2C, and 2D), and/or whether electrode 128 and a portion of loop portion 130 extends distally of outer sheath 112 (FIG. 2E).

Medical device 100 may be inserted into a body lumen of a subject, either through an insertion device (not shown) or alone, such that at least a portion of shaft 104 may be within the subject, while handle 102 may remain outside of the subject. Distal end 106 may be positioned at a target site within the subject (e.g., within a portion of a gastrointestinal (GI) tract). From outside of the subject, a user may manipulate handle 102. Movement of movable body 110 relative to main body 108 in a first direction (e.g., the distal direction) may extend end effector 126 (e.g., electrode 128) relative to shaft 104 (e.g., move end effector 126 distally relative to outer sheath 112 and the distal end of shaft 104). The end cap 114 may remain at least partially within outer sheath 112 to as to seal an area external of/distal to outer sheath 112 from any fluid passing through outer sheath 112. Further movement of movable body 110 relative to main body 108 in the first direction (e.g., the distal direction) may further extend end effector 126 (e.g., electrode 128 and loop portion 130) relative to shaft 104. In some aspects, loop portion 130 may expand (e.g., radially outward) when extended distally of shaft 104 (e.g., distally of one or more of outer sheath 112 and/or inner sheath 116. Additionally, movement of movable body 110 relative to main body 108 in a second direction (e.g., the proximal direction) may retract end effector 126 (e.g., electrode 128 and loop portion 130) relative to shaft 104 (e.g., move electrode 128 proximally relative to a distal end of shaft 104). For example, in some aspects, loop portion 130 may contract (e.g., radially inward) when retracted within and/or proximal of shaft 104. Although not shown, movable body 110 or additional components of handle 102 may articulate end effector (or end effector 126 and distal end 106) left or right, and/or up or down relative to shaft 104. Furthermore, although not shown, a portion of shaft 104 may be positioned within a lumen of an insertion device (e.g., a scope), and a distal portion of the insertion device may be deflectable to help direct end effector 126 and distal end 106.

Referring now to FIGS. 1A and 1B, main body 108 may include a slot 134, and movable body 110 may be slidably positioned within slot 134. Additionally, handle 102 may be configured to held and manipulated by an operator's hand. In these aspects, main body 108 may be configured to be held by a user's hand, and may include a thumb ring 136 (e.g., at a proximal end of main body 108). Additionally, movable body 110 may include one or more (e.g., two) finger holes 138, such that movement of one or more fingers relative to the operator's thumb controls the position of movable body 110 relative to main body 108, and thus also controls the position of end effector 126 relative to shaft 104 and distal end 106. Alternatively, although not shown, the arrangement of main body 108 and movable body 110 may be reversed, for example, with main body 108 including one or more finger holes 138 and movable body 110 including a thumb ring 136.

As mentioned, movable body 110 may be coupled to control wire 132 to control the movement and/or position of end effector 126. A portion of movable body 110 may be coupled to a proximal end of control wire 132, for example, within slot 134. Moreover, in some examples, control wire 132 may be conductive, for example, electrically connecting hub 124 to end effector 126, such that energy from an energy source (not shown) may be delivered to end effector 126. For example, hub 124 may include one or more pins or prongs to couple to the energy source. The energy source may be electrocautery source, a radio frequency generator, a heating source, a current generator, etc. In one aspect, medical device 100 may be used for monopolar electrosurgery, and may include a return electrode positioned remotely from electrode 128 on or otherwise adjacent to the subject. In another aspect, medical device 100 may be used for bipolar electrosurgery. In that instance, electrode 128 may include an active electrode portion, and a return electrode may be provided at or near another portion of electrode 128 and/or shaft 104. In one example, although not shown, two conductive elements may run through shaft 104, where the conductive elements may be electrically isolated from each other, allowing one to conduct energy to the active electrode and the other to conduct energy from a return electrode. Although not shown, in another aspect, the energy source may be a part of handle 102 (e.g., an internal battery in handle 102).

Movable body 110 may be lockable or otherwise at least partially or temporarily secured in one or more positions relative to main body 108. For example, a portion of main body 108 (e.g., a lateral side portion, adjacent to a side that defines slot 134) may include a plurality of contours 140 (e.g., serrations, grooves, extensions, recesses, etc.). Contours 140 may be arranged in a row to form a contoured surface 142. Moreover, movable body 110 may include one or more detents 144 (e.g., pins, prongs, extensions, etc.). The one or more detents 144 may extend radially inward from an internal portion of movable body 110, for example, to engage or otherwise interact with contours 140 on main body 108. In some aspects, the one or more detents 144 may be biased (e.g., spring biased, cantilevered, etc.) to at least partially secure the position of movable body 110 relative to main body 108. For example, the biasing may help to require a minimum or necessary amount of operator force to overcome the interaction of detent 144 and contours 140 in order to move movable body 110 (e.g., proximally or distally) relative to main body 108. In some aspects, only one side (e.g., a left side) of handle 102 (e.g., main body 108 and movable body 110) include contoured surface 142 and one or more detents 144. In other aspects, more than one side (e.g., left and right sides) of handle 102 (e.g., main body 108 and movable body 110) include contoured surface 142 and one or more detents 144.

Although not shown, one or more portions of handle 102 may include one or more markings (e.g., visual markings, tactile markings, etc.). For example, one or more markings on main body 108 may correspond to a position of movable body 110 in which end effector 126 is fully retracted relative to shaft 104. Additionally, one or more markings on main body 108 may correspond to a position of movable body 110 in which end effector 126 is partially extended relative to shaft 104, for example, such that electrode 128 is extended from shaft 104 and loop portion 130 is retained within shaft 104. Furthermore, one or more markings on main body 108 may correspond to a position of movable body 110 in which end effector 126 is fully extended relative to shaft 104, for example, such that electrode 128 and loop portion 130 are extended from shaft 104.

Figure 2A:
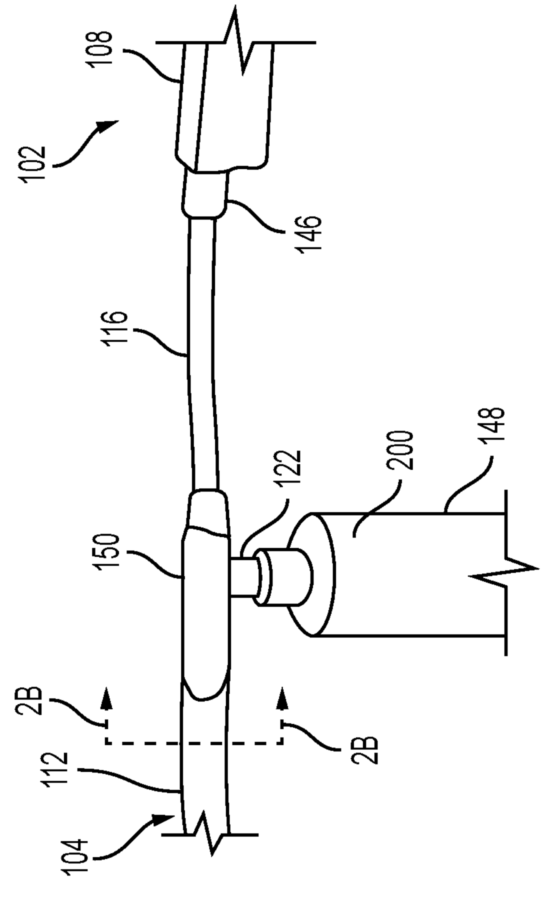

FIGS. 2A-2E illustrate various additional features of medical device 100. FIG. 2A illustrates various features of a proximal portion of medical device 100. As shown in FIG. 2A, a distal portion of main body 108 of handle 102 may be coupled to inner sheath 116, for example, via a coupler 146, which may help to secure inner sheath 116 to handle 102. Inner sheath 116 may surround at least a portion of control wire 132 (FIG. 2C). Furthermore, as mentioned above, end effector 126 may be movable relative to outer sheath 112 and shaft 104, as shown in FIGS. 2C-2E.

Medical device 100 may include fluid port 122. For example, fluid port 122 may be couplable to a fluid source 148, for example, a syringe, a pump (not shown), a reservoir, etc., containing a fluid 200. Fluid port 122 may be coupled to a fluid hub 150. Fluid hub 150 may at least partially surround inner sheath 116, for example, at a position distal to or spaced from coupler 146. Fluid hub 150 (e.g., a distal portion of fluid hub 150) may be coupled to outer sheath 112. One or more of fluid port 122 and fluid hub 150 may include a one-way valve, a luer, a seal, threading, and/or any appropriate element to help maintain a secure connection between shaft 104 and fluid source 148, minimize or prevent back-flow (e.g., fluid flowing proximally out of port 122 toward fluid source 148), and/or minimize or prevent leakage. In these aspects, fluid 200 delivered from fluid source 148 (e.g., syringe) may be delivered through fluid port 122, fluid hub 150, and into a shaft cavity 152 (FIG. 2B) between inner sheath 116 and outer sheath 112. Accordingly, shaft 104 may deliver fluid to the treatment site. Additionally, inner sheath 116 may help insulate the fluid delivered through shaft cavity 152 between inner sheath 116 and outer sheath 112 from energy being delivered by control wire 132. As mentioned above, a distal end of inner sheath 116 may abut or be positioned adjacent to proximal face 114B of end cap 114 when end cap 114 is retracted and at least partially positioned within outer sheath 112, but end cap 114 is movable relative to inner sheath 116.

Figure 2B:
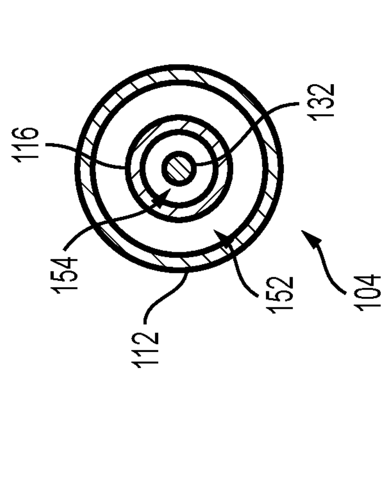

For example, FIG. 2B is a lateral cross-sectional view of a portion of FIG. 2A along line 2B-2B. As shown, inner sheath 116 at least partially surrounds control wire 132. Moreover, outer sheath 112 surrounds and is spaced away from inner sheath 116, forming shaft cavity 152. In some aspects, outer sheath 112 and inner sheath 116 maybe coaxial. Moreover, in some aspects, inner sheath 116 surround and may be spaced away from control wire 132, for example, forming a wire cavity 154. Alternatively, although not shown, an inner portion of inner sheath 116 may abut an outer portion of control wire 132. For example, inner sheath 116 may be an insulating coating on at least a portion of control wire 132.

FIGS. 2C-2E illustrate various distal features of distal end 106 of medical device 100. As shown, end effector 126, including electrode 128 and loop portion 130, and end cap 114 may be positioned with outer sheath 112 of shaft 104. In some aspects, end cap 114 may be formed of rubber or another biocompatible and at least partially flexible material. In some aspects, end cap 114 may be fixedly coupled to electrode 128 (e.g., to a proximal portion of electrode 128). Alternatively, in other aspects, electrode 128 may be at least partially movable relative to end cap 114. In either aspect, end cap 114 may be positioned within a portion of outer sheath 112 to form a distal cavity 156. Additionally, inner sheath 116 may terminate proximal of end cap 114, for example, adjacent to a portion of loop portion 130. Accordingly, shaft cavity 152 may be fluidly connected to distal cavity 156.

As shown in FIGS. 2C and 2D, electrode 128 includes an electrode shaft 128A. FIG. 2C illustrates internal components of distal end 106, and FIG. 2D illustrates a cross-sectional view of electrode 128 illustrating the flow of fluid 200. Additionally, FIG. 2E illustrates a perspective view of distal end 106 in another configuration, for example, with end effector 126 extended from shaft 104 and outer sheath 112. In some aspects, electrode 128 may include a distal end portion 128B, which may be wider than electrode shaft 128A, for example, extending radially relative to a longitudinal axis of electrode 128. Moreover, electrode shaft 128A (e.g., a proximal portion of electrode shaft 128A includes one or more inlets 158, for example, two inlets 158. Inlets 158 may be formed, for example, on a radially outer surface of electrode shaft 128A. As mentioned, electrode 128 includes an electrode lumen 128C, for example, terminating distally at electrode outlet 128D. A proximal end of electrode 128 may be closed, for example, by being fixed to the distal end of loop portion 130. Accordingly, fluid 200 delivered through shaft cavity 152 may flow into distal cavity 156, and then through inlets 158, through the electrode lumen 128C, and out of electrode outlet 128D. In at least some aspects, inner sheath 114 may help to cover and/or insulate control wire 132 and loop portion 130 when control wire 132 and loop portion 130 are retracted proximally.

Moreover, as shown in FIG. 2E, end effector 126 may be extended distally of outer sheath 112. For example, movement of movable body 108 (FIGS. 1A and 1B) may move control wire 132 through inner sheath 116 to extend end effector 126 from outer sheath 112. In these aspects, loop portion 130 may be extended distal to outer sheath 112, and loop portion 130 may expand. In some aspects, as shown in FIG. 2E, loop portion 130 may abut a portion (e.g., proximal face 114B, FIGS. 2C and 2D) of end cap 114 when end effector 126 is advanced distally, urging end cap 114 distally and out of outer sheath 112. In other aspects, loop portion 130 may be movable relative to end cap 114, for example, through opening 114A of end cap 114. In these aspects, loop portion 130 may expand when extended distally. Moreover, loop portion 130 may be energized (e.g., via hub 124 and control wire 132), for example, for resection of tissue or one or more other areas of the treatment site.

It is noted that, in other embodiments, end cap 114, inlets 158, electrode lumen 128C and electrode outlet 128D are not included. For example, instead of fluid being delivered through electrode 128, the fluid may be delivered around electrode 128. In some aspects, however, electrode 128 (e.g., electrode shaft 128A) may help to guide the fluid to the treatment site, for example, via capillary action.

As mentioned, electrode 128 and loop portion 130 are be formed of a conductive material, for example, a stainless steel (e.g., 316 L stainless steel), titanium, or another medically-safe and conductive material. In some aspects, one or more of electrode 128 and loop portion 130 may include a surface finish, for example, may be passivated per ASTM A967 Nitric 2.

As discussed above, medical device 100, including end effector 126, may be used to deliver energy and/or fluid to a treatment site. For example, distal end 106 may be delivered to the treatment site, for example, via a working channel of an insertion device (e.g., a scope). End effector 126 may be positioned at least partially within outer sheath 112, for example, as shown in FIGS. 1A, 2C, and 2D. As shown, distal portion 128B of electrode may extend distal to outer sheath 112 and end cap 114, but inlet 158 and a proximal portion of electrode shaft 128A are positioned proximal of end cap 114 and within outer sheath 112. In other aspects, distal portion 128B (e.g., a proximal face of distal portion 128B) may abut distal end 114C of end cap 114 when medical device 100 is delivered to the treatment site, and a portion of electrode 128 may be extended distally of end cap 114 (e.g., via movement of movable body 108) once distal end 106 is at the treatment site. Alternatively, electrode 128 may not include a widened distal portion 128B, and an entirety of electrode 128 may be proximal of end cap 114 (e.g., within shaft 104) during delivery to the treatment site, and then electrode 128 may be extended through opening 114A of end cap 114. In these aspects, with a portion of electrode 128 distal to end cap 114, electrode 128 may be energized, for example, with energy being delivered through hub 124, control wire 132, and loop portion 130 to electrode 128. One or more portions of electrode 128 may be applied to tissue or other portions of the treatment site, for example, to cut one or more layers of tissue.

Additionally or alternatively, with a portion of electrode 128 extending proximal of end cap 114, medical device 100 may be used to deliver fluid to the treatment site. For example, fluid 200 from fluid source 148 may be delivered through shaft cavity 152. Fluid 200 may flow from shaft cavity 152 into distal cavity 156. With end cap 114 forming a seal at a distal portion of outer shaft 112, fluid 200 may flow from distal cavity 156 into electrode lumen 128C via one or more inlets 158. Fluid 200 may then flow through electrode lumen 128C and out of electrode outlet 128D. In some aspects, the user may energize electrode 128 to cut one or more layers of tissue, and may then position distal end 128B of electrode 128 between layers of tissue. The user may then deliver fluid through electrode 128, as discussed above, to deliver fluid between the layers of tissue. The fluid between the layers of tissue may help to separate the layers of tissue, elevate one or more upper layers of tissue, form a bleb, etc. The user may then energize electrode 128 again, for example, to further cut tissue or one or more other portions of the treatment site.

The user may also extend end effector 126 distally, for example, by advancing movable body 108 distally. In these aspects, loop portion 130 may abut proximal face 114B of end cap 114 and may urge end cap 114 distally and out of outer sheath 112, exposing at least a portion of loop portion 130 distal to outer sheath 112, as shown in FIG. 2E. Alternatively, loop portion 130 may be advanced distally through opening 114A of end cap 114 in order to expose loop portion 130 distal to outer sheath 112. In either aspect, exposing loop portion 130 may transition loop portion 130 from a collapsed configuration to an expanded configuration. Moreover, with loop portion 130 exposed, end effector 126 may be energized, for example, via hub 124 and control wire 132. Loop portion 130 may be applied to tissue or one or more other portions of the treatment site, for example, to resect the tissue or the other portion(s) of the treatment site.

End effector 126 may be removed proximally, for example, to remove the resected tissue or other portion(s) of the treatment site. Alternatively, the user may extend end effector 126 distally, for example, to expose and expand loop portion 130 to release the resected tissue or other portion(s) of the treatment site. The user may manipulate handle 102, movable body 108, or the insertion device in order to position end effector 126 throughout these steps. Additionally, the aforementioned steps may be performed as many times as needed to treat the treatment site. For example, end effector 126 may be retracted proximally to reposition end cap 114 within outer sheath (e.g., as shown in FIGS. 2C and 2D), allowing for the user to deliver fluid through electrode 128 again. Moreover, the aforementioned steps may be repeated and/or performed in various orders to treat the treatment site, and/or one or more of the aforementioned steps may be omitted during the treatment.

Figures 3A, 3B:
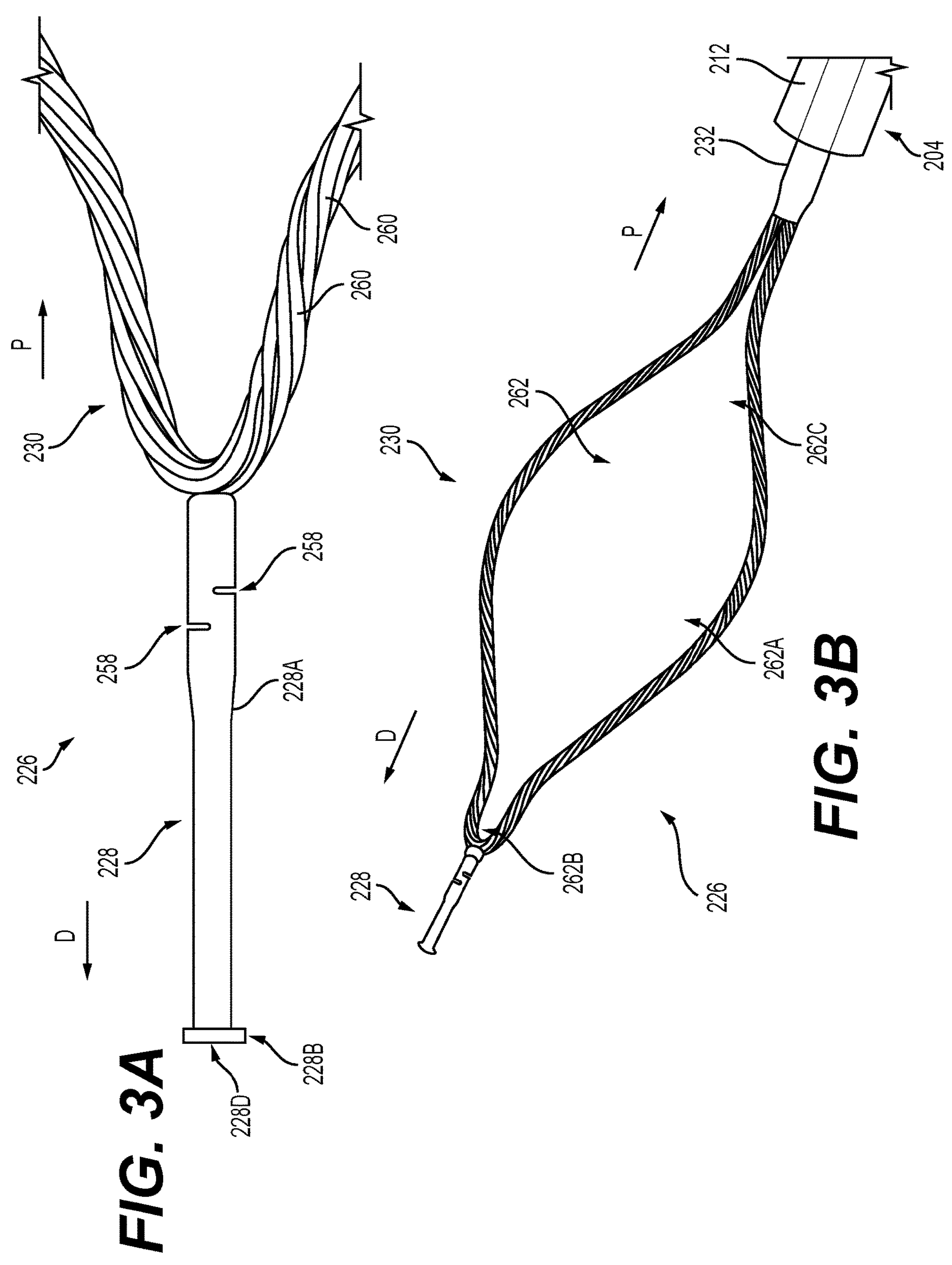
FIGS. 3A-3D illustrate various views of portions of another multifunctional end effector of the medical device, according to aspects of this disclosure.

FIGS. 3A-3D illustrate additional features of a multifunctional end effector 226. FIG. 3A is an enlarged view of a distal portion of end effector 226, including an electrode 228 and a distal portion of a loop portion 230. As shown, electrode 228 includes one or more inlets 258 in a portion (e.g., a proximal portion) of electrode shaft 228A, and electrode 228 include a widened distal end 228B. In some aspects, electrode 228 includes two inlets 258, with the inlets 258 being longitudinally spaced apart on electrode shaft 228A. Moreover, the inlets 258 may be positioned on opposing sides of electrode shaft 228A. As discussed above, electrode 228 may include an electrode lumen (not shown) that fluidly couples inlet(s) 258 to an electrode outlet 228D to deliver fluid through electrode 228.

As shown in FIGS. 3A and 3B, loop portion 230 may be formed of one or more conductive materials, for example, in the shape of a coil, intertwined wires or strands 260, one or more wires, etc. In some aspects, loop portion 230 may be formed of a shape memory material (e.g., Nitinol), such that when loop portion 230 is extended from shaft 204 (e.g., from outer sheath 212), loop portion 230 expands to an at least partially expanded configuration. As shown in FIG. 3B, the expanded configuration may be at least partially tear dropped shape, for example, to form a snare loop. In some aspects, loop portion 230 forms an aperture 262, and aperture 262 may have a wide portion 262A and a tapered or narrowed portion 262B, for example, toward a distal end of loop portion 230. Aperture 262 may also have another tapered or narrowed portion 262C, for example, to a proximal end of loop portion 230. Furthermore, a proximal end of loop portion 230 is coupled to a distal end of control wire 232. In some aspects, a portion of loop portion 230 may be surrounded by or otherwise overlap with a portion of control wire 232.

In any of these aspects, a proximal end of electrode 228 is fixedly coupled to a distal end of loop portion 230. For example, the proximal end of electrode 228 may be welded to the distal end of loop portion 230. Accordingly, energy (e.g., electrical energy), may be delivered from control wire 232 to electrode 228 through loop portion 230.

Figures 3C, 3D:
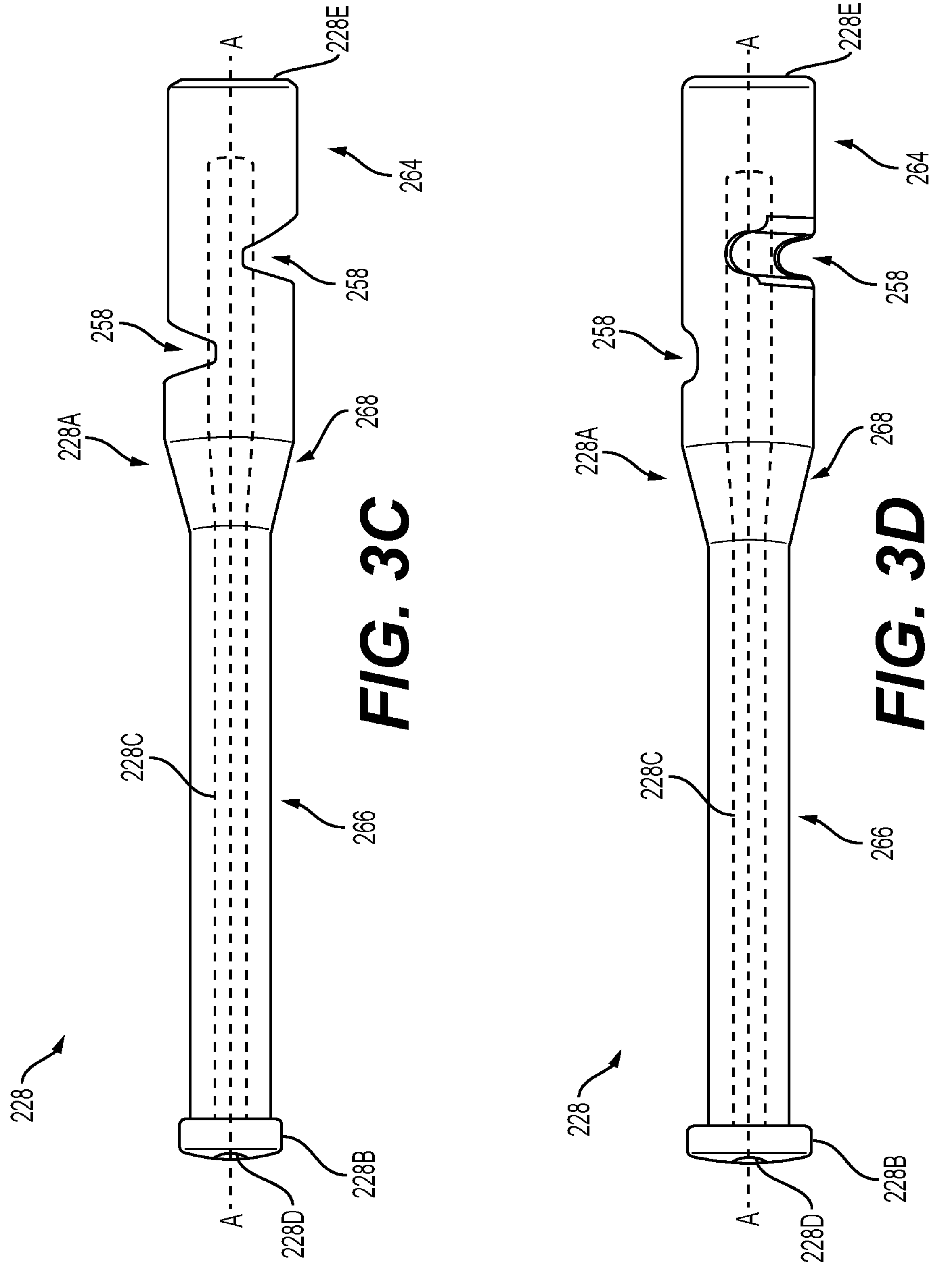

FIGS. 3C and 3D are different side views of electrode 228. For example, FIG. 3C is a side view of electrode 228 in a first orientation, and FIG. 3D is a side view of electrode 228 rotated (e.g., around longitudinal axis A) compared to FIG. 3C. As mentioned above, electrode 228 includes electrode shaft 228A and distal end 228B (e.g., a widened distal end). Electrode 228 includes electrode lumen 228C extending longitudinally through at least a portion of electrode 228, for example, fluidly connecting inlets 258 to electrode outlet 228D. Moreover, as shown, electrode lumen 228C may not extend proximally to proximal end 228E of electrode 228. Instead, proximal end 228E of electrode 228 may be closed, and may be coupled (e.g., welded) to the distal end of loop portion 230, as discussed above with respect to FIGS. 3A and 3B.

Electrode shaft 228A may include a first or proximal longitudinal portion 264 ("proximal portion 264") and a second or distal longitudinal portion 266 ("distal portion 266"), for example, with an angled or tapered portion 268 between proximal portion 264 and distal portion 266. As shown, inlets 258 may be positioned in proximal portion 264. Moreover, in some aspects, although not shown, an end cap may be coupled to or otherwise positioned on electrode shaft 228A on or adjacent to tapered portion 268, for example, on a portion of distal portion 266 adjacent to tapered portion 268. In some aspects, electrode 228 may be movable relative to the end cap. In these aspects, tapered portion 268 may at least partially engage with the end cap. For example, as electrode 228 is advanced distally, electrode 228 may move within the opening of the end cap. However, when tapered portion 268 engages with the end cap, electrode 228 may urge the end cap distally, for example, out of the outer sheath. With the end cap uncoupled from the outer sheath, electrode 228 may continue to be advanced distally, for example, exposing loop portion 230 from the shaft.

Figures 4A, 4B, 4C:
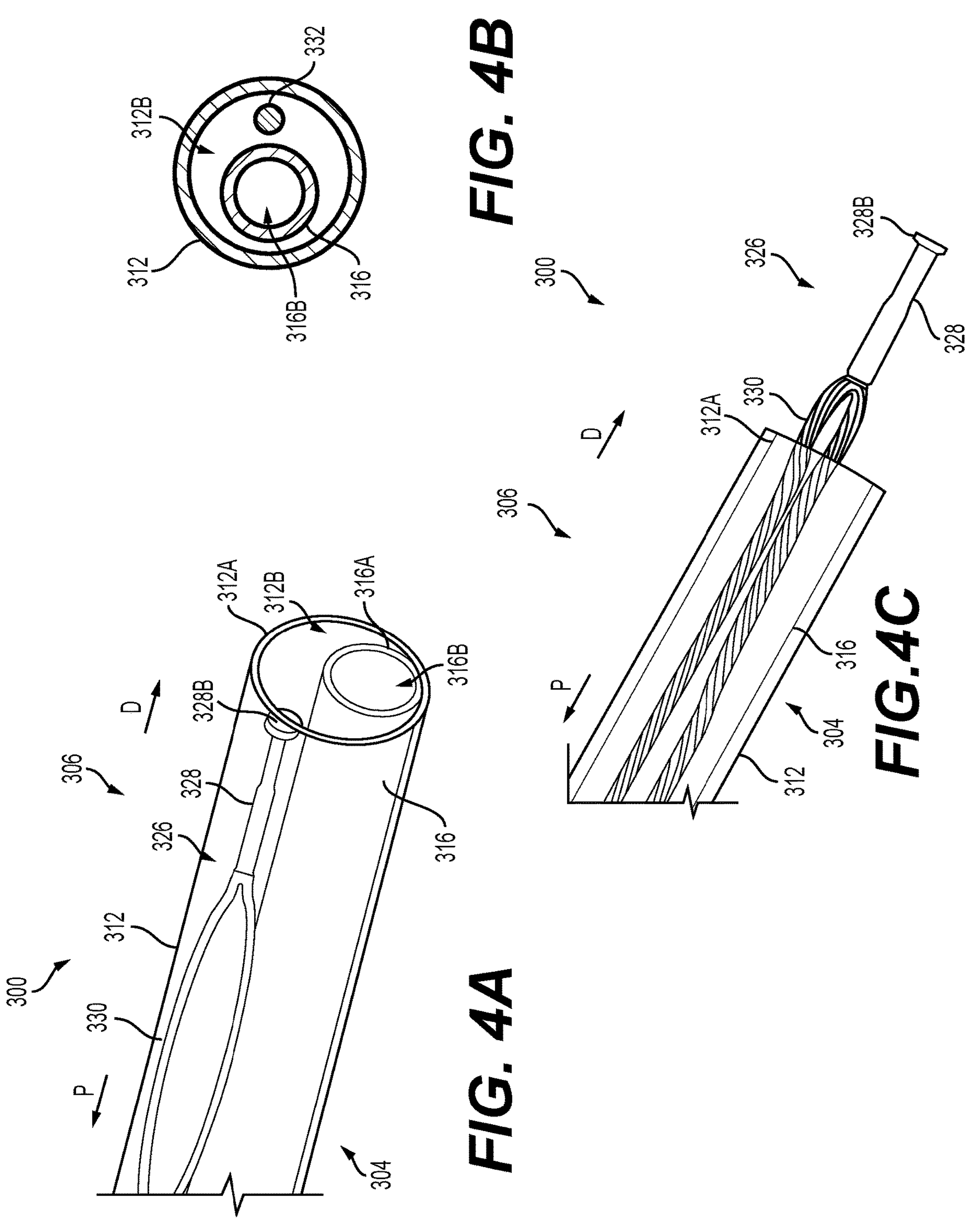
FIGS. 4A-4C illustrate various views of portions of an additional exemplary medical device with a multifunctional end effector, according to aspects of this disclosure.

FIGS. 4A-4C illustrate various aspects of another medical device 300. Medical device 300 includes a shaft 304 with a distal end 306. Although not shown, shaft 304 may be coupled to a handle, for example, similar to handle 104, as discussed above. Shaft 304 includes an outer sheath 312 and an inner sheath 316, for example, similar to the sheaths discussed above. Moreover, medical device 300 includes a multifunctional end effector 326, including an electrode 328 and a loop portion 330. As shown in FIG. 4A, end effector 326 may be positioned within outer sheath 312, for example, adjacent to inner sheath 316. Stated another way, end effector 326 is not positioned radially within inner sheath 316, and end effector 326 may extend alongside inner sheath 316, with a longitudinal axis of end effector 326 and/or control wire 332 (see FIG. 4B) being approximately parallel to a longitudinal axis of inner sheath 316. Moreover, a distal end 316A of inner sheath 316 may be aligned with and/or in proximity to a distal end 312A of outer sheath 312. In some aspects, a portion of inner sheath 316 may be coupled (e.g., via a laser weld, an adhesive, etc.) to a portion of outer sheath 312. For example, an exterior portion of inner sheath 316 may be coupled to an interior portion of outer sheath 312 (e.g., over at least a portion of the longitudinal length or a distal portion of inner sheath 316).

For example, FIG. 4B illustrates a cross-sectional view of a proximal portion of shaft 304. As shown, a control wire 332, which may control the movement and/or position of end effector 326 and/or deliver energy to end effector 326, may be positioned within a lumen 312B of outer sheath 312 adjacent to inner sheath 316. A proximal end of outer sheath 312 may be fixedly coupled to a distal end of a handle, for example, to a main or fixed body of the handle. A proximal end of control wire 332 may be coupled to a movable body of the handle, as discussed above. Additionally, a proximal end of inner sheath 316 may be coupled (e.g., movably or fixedly) to another portion of medical device 300, for example, to a port adjacent to the handle (e.g., FIG. 2A), to a port on the main body of the handle, etc. Inner sheath 316 includes a lumen 316B, which may receive fluid through the port.

In these aspects, end effector 326 may be movable relative to shaft 304. For example, as shown in FIG. 4A, end effector 326 may be positioned within outer sheath 312 during the delivery and/or positioning of distal end 306 at the treatment site. Then, as shown in FIG. 4C, one or more portions of end effector 326 may be extended distal to shaft 304. For example, electrode 328 may be extended distal to distal end 312A of outer sheath 312 via distal movement of control wire 332. Electrode 328 may be energized, for example, via control wire 332 and loop portion 330 to cut tissue. Further distal movement of control wire 332 may also extend loop portion 330 from outer sheath 312. Loop portion 330 may be energized, for example, via control wire 332 for resection of tissue (e.g., a lesion). The movement of end effector 326 may be controlled via one or more portions (e.g., a movable body) of the handle coupled to a proximal end of shaft 304. As shown in FIG. 4A, a distal end 328B of electrode 228 may be closed or solid, for example, not including an outlet. Nevertheless, end effector 326 may be energized (e.g., via control wire 332) to deliver energy to the treatment site, with one or more of electrode 328 and/or loop portion 330.

Moreover, fluid may be delivered to the treatment site via inner sheath 316, for example, via inner sheath lumen 316B. In this aspect, the fluid may be delivered to inner sheath 316 as discussed above, for example, with respect to FIG. 2A. Additionally, the fluid may be delivered contemporaneously with energy delivery via end effector 326, or the fluid may be delivered in an alternating manner with energy delivery via end effector 326. For example, end effector 326 may be retracted within outer sheath 312 (e.g., such that distal end 328B of electrode 328 is proximal of distal end 312A of outer sheath 312) during the delivery of fluid via inner sheath 316. Retracting end effector 326 during fluid delivery may help to avoid or minimize interference with the delivery of the fluid. Furthermore, in some aspects, although not shown, inner sheath 316 may be movable relative to outer sheath 312, for example, to extend inner sheath 316 distal to distal end 312A of outer sheath 312.

Additionally, although not shown, one or more portions of control wire 332 may be coated with an insulating material. For example, the insulating coating on control wire 332 may take the place and/or functionality of the inner sheath. In some aspects, the insulating coating on control wire 332 may help to isolate the electrically charged wire from the fluid being delivered to the treatment site. In these aspects, medical device 300 may still include inner sheath 316, for example, to help deliver the fluid to the treatment site. Alternatively, in other aspects, medical device 300 may not include inner sheath 316, with fluid being delivered through outer sheath 312. The fluid may be delivered around electrode 328 and end effector 326. In a further alternative, as in FIGS. 2C and 2D, distal end 306 includes an end cap and electrode 328 includes inlets and a lumen connecting to an outlet, such that fluid may be delivered to the treatment site through the electrode.

Figures 5, 6:
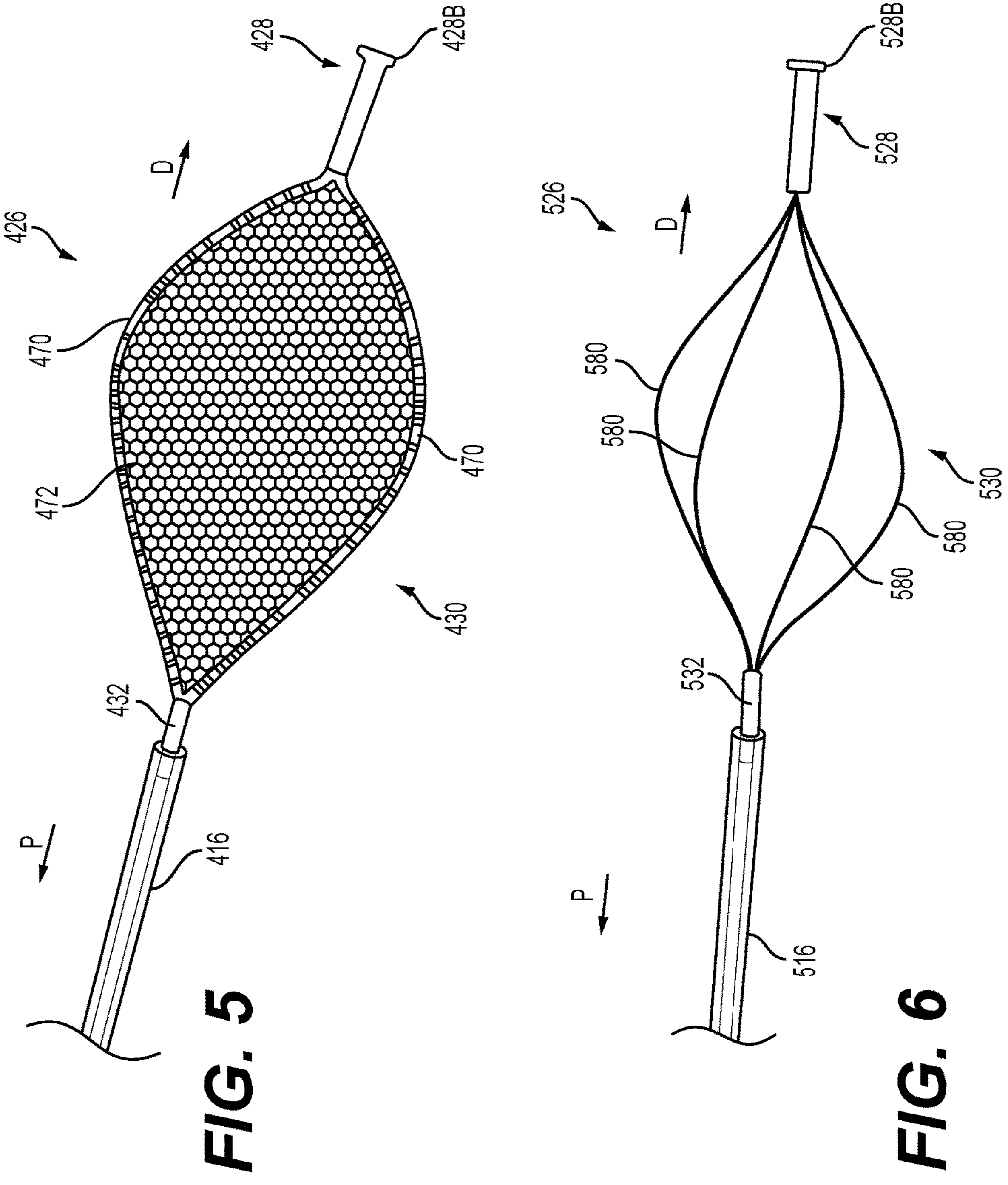
FIG. 5 is a side view of a distal end of another exemplary medical device including a multifunctional end effector, according to aspects of this disclosure.
FIG. 6 is a side view of a distal end of yet another exemplary medical device including another multifunctional end effector, according to aspects of this disclosure.

FIG. 5 illustrates an end effector 426 that may be used with any of the medical devices discussed herein. End effector 426 includes an electrode 428, for example, including a widened distal portion 428B. End effector 426 also includes a loop portion 430, for example, with a distal end of the loop portion 430 coupled to a proximal end of electrode 428, as discussed above. Loop portion 430 includes two arms 470, which may be expandable and/or contractible, as discussed above. Furthermore, as shown in FIG. 5, loop portion 430 includes a netting 472. Netting 472 may be a retrieval net, which, in some aspects, is nonconductive. In these aspects, electrode 428 and/or arms 470 of loop portion 430 may be energized to cut, resect, or otherwise treat tissue. Moreover, netting 472 may be positioned to capture or otherwise retain tissue or other material (e.g., tissue or material separated from the treatment site). For example, loop portion 430 may be energized to resect tissue or material, and netting 472 may help to capture the resected tissue or material. Retracting end effector 426 may contract loop portion 430, and the contracted loop portion 430 and netting 472 may help to retain the resected tissue or material.

End effector 426 may be movably controlled by movement of a control wire 432. As discussed above, control wire 432 may be coupled to a movable body of a handle (not shown) in order to control the movement and/or position of end effector 426. Moreover, in some aspects, control wire 432 may be at least partially covered and/or insulated by a sheath 416. Although not shown, a portion of end effector 426 (e.g., electrode 428) may be coupled to and/or extend through an end cap, as discussed above. End effector 426 may include a shape and/or material of one or more of end effectors 126, 226, 326 discussed above. Additionally, a portion of end effector 426 (e.g., electrode 428) may include one or more inlets, an internal lumen, and an outlet, as discussed above, in order to deliver fluid to a treatment site.

FIG. 6 illustrates another end effector 526 that may be used with any of the medical devices discussed herein. End effector 526 includes an electrode 528, for example, including a widened distal portion 528B. End effector 526 also includes a loop portion 530, for example, with a distal end of the loop portion 530 coupled to a proximal end of electrode 528, as discussed above. Loop portion 530 includes a plurality of wires 580 (e.g., three or more wires), which may be expandable and/or contractible, as discussed above. In an expanded configuration, plurality of wires 580 may form a basket shape. Each of wires 580 may be formed of one or more conductive materials, for example, in the shape of a coil, intertwined wires or strands, one or more wires, etc., and may be formed of a shape memory material (e.g., Nitinol). As shown in FIG. 6, loop portion 530 may include four wires 580. Nevertheless, loop portion 530 may include fewer or more wires 580, and wires 580 may be evenly or unevenly spaced, for example, in the expanded configuration. One or more of wires 580 are conductive, for example, to convey energy from a control wire 532 to electrode 528. In these aspects, electrode 528 and/or one or more wires 580 of loop portion 530 may be energized to cut, resect, or otherwise treat tissue. Moreover, wires 580 of loop portion 430 may be positioned to capture or otherwise retain tissue or other material (e.g., tissue or material separated from the treatment site). For example, loop portion 530 may be energized to resect tissue or material, and wires 580 may help to capture the resected tissue or material. Retracting end effector 526 may contract loop portion 530, and the contracted wires 580 of loop portion 530 may help to retain the resected tissue or material.

End effector 526 may be movably controlled by movement of control wire 532. As discussed above, control wire 532 may be coupled to a movable body of a handle (not shown) in order to control the movement and/or position of end effector 526. Moreover, in some aspects, control wire 532 may be at least partially covered and/or insulated by a sheath 516 or an insulating coating. Although not shown, a portion of end effector 526 (e.g., electrode 528) may be coupled to and/or extend through an end cap, as discussed above. End effector 526 may include a shape and/or material of end effectors 126, 226, 326 discussed above. Additionally, a portion of end effector 526 (e.g., electrode 528) may include one or more inlets, an internal lumen, and an outlet, as discussed above, in order to deliver fluid to a treatment site.

Figure 7:
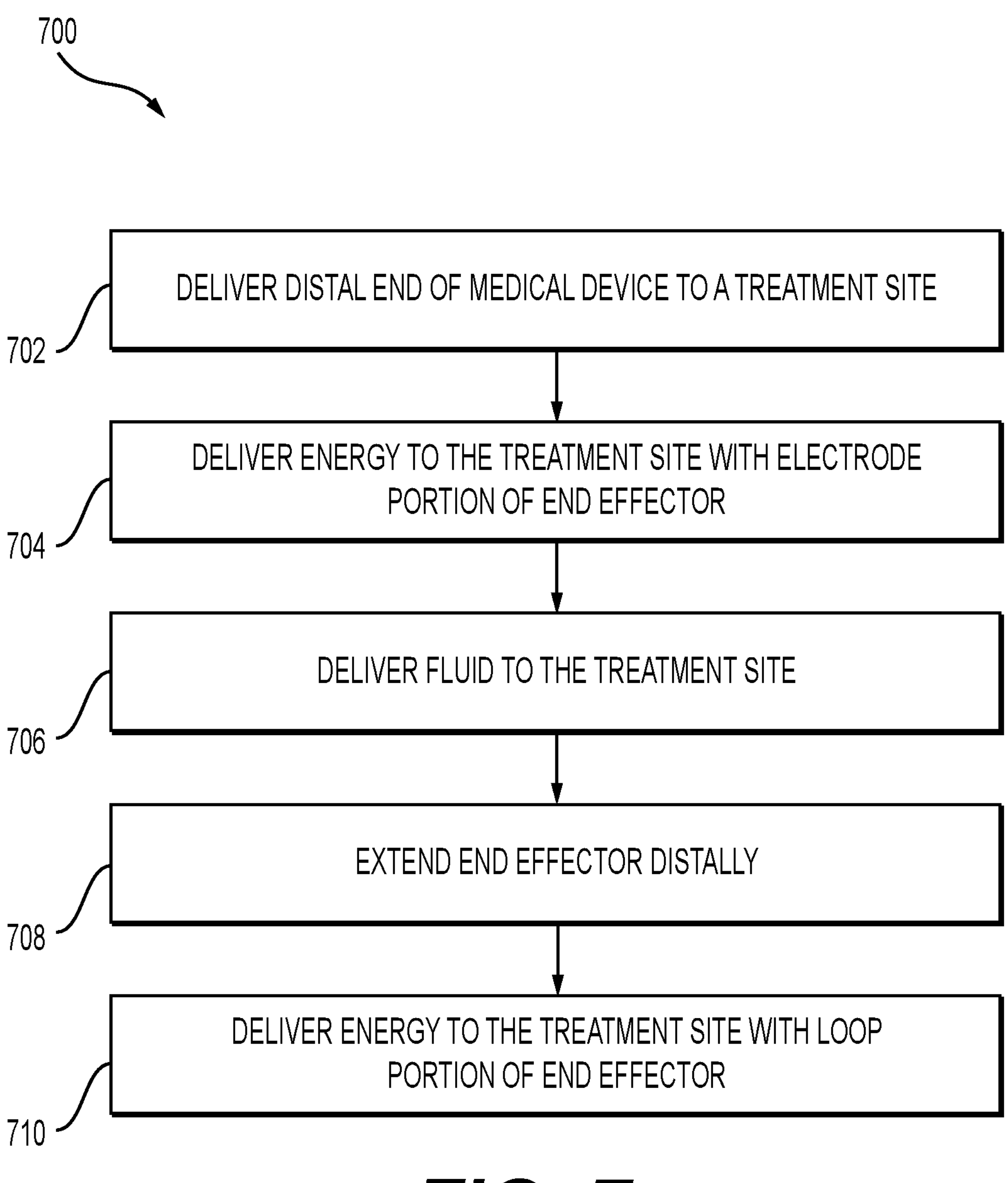
FIG. 7 is a flow diagram of an exemplary method, according to aspects of this disclosure.

FIG. 7 illustrates a method 700 that may be performed with any of the medical devices or portions of the medical devices discussed herein. Specifically, method 700 includes an initial step 702 that includes delivering the distal end of the medical device to a treatment site. Shaft 104 may be delivered to the treatment site via an insertion device (e.g., an endoscope, insertion device, sheath, etc.). In some aspects, a distal portion of the insertion device may be deflectable, for example, to help position distal end 106 of medical device 100 to the treatment site. Additionally, step 702 may include positioning distal end 106 at the treatment site. Step 702 may include extending movable body 110 distally relative to main body 108, for example, to extend control wire 132 and end effector 126 distally. Furthermore, detent 144 and contoured surface 142 may help to control and/or lock the position of (e.g., lockably position) movable body 110 on main body 108.

Next, method 700 includes a step 704 that includes delivering energy to the treatment site with the electrode portion of the end effector. As mentioned, energy may be delivered via hub 124, through control wire 132, though loop portion 130, and to electrode 128. Moreover, step 702 may include only a portion of electrode 128 being extended distally of end cap 114 or otherwise distally from shaft 104. Step 704 may be performed to cut one or more layers of tissue at the treatment site.

Method 700 also includes a step 706 that includes delivering fluid to the treatment site. Step 706 may include delivering fluid from fluid source 148, through shaft cavity 152, and into distal cavity 156. As discussed, electrode 128 may include one or more inlets 158, and fluid in distal cavity 156 may flow through inlets 158, through electrode lumen 128C, and out of electrode outlet 128D. In these aspects, end cap 114 may help to seal distal cavity 156, such that fluid only flows through electrode 128 and not out of outer sheath 112. Step 706 may be performed with a distal portion of electrode 128 positioned within tissue (e.g., between layers of tissue). In this aspect, step 706 may include delivering fluid within the tissue, for example, to separate layers of tissue and/or to form a bleb. In some aspects, step 706 may include repositioning end effector 126. For example, as discussed with respect to FIGS. 4A-4C, step 706 may include retracting end effector 326, and delivering fluid through inner sheath 316.

Next, a step 708 include extending end effector distally. As discussed above, end effector 126 includes loop portion 130, and extending end effector 126 distally may expose at least a portion of loop portion 130. When exposed, at least a portion of loop portion 130 may expand. Additionally, as discussed above, extending end effector 126 distally may help to extend end cap 114 distally, allowing for loop portion 130 to be exposed. Alternatively, loop portion 130 may be advanced through opening 114A of end cap 114 in order to expose loop portion 130.

Furthermore, a step 710 includes delivering energy to the treatment site with the loop portion of the end effector. As discussed, loop portion 130 is conductive, and may deliver energy to the treatment site, for example, for resection. The loop portion may include netting 472 supported by arms 470 (FIG. 5), or may include a plurality of wires 580, for example, to help retain tissue or material.

Moreover, various steps of method 700 may be repeated as many times as needed to treat the treatment site. Furthermore, in some aspects, medical device 100 may be removed from the treatment site (e.g., through a lumen or working channel of an insertion device), and another medical device may be delivered to further treat the treatment site.

The various end effectors discussed herein are capable of modifying physical properties of tissue when in contact with tissue by delivering energy (e.g., radio frequency energy). The energy delivered may be monopolar or bipolar energy. The various end effectors may be coupled to a shaft, with the shaft configured to extend into a body lumen or cavity of a subject. The shaft includes an electrical element traversing the shaft and connecting the electrode to an energy source, for example, in the handle or coupled to the handle.

As discussed, the end effectors may also be coupled to an actuation member (e.g., movable body 110), for example, in the handle or coupled to the handle, that allows a user to translate the end effectors relative to the shaft. The end effectors may be translatable between at least a first position in which a cutting shaft (e.g., electrode shaft 128A), of the end effectors is retracted within the shaft, and a second position in which the cutting shaft is extended beyond the shaft and exposed. Moreover, the end effectors may be positioned in a third position in which the loop portion is extended beyond the shaft and exposed. Additionally, the end effectors or medical devices may be used to deliver fluid to the treatment site, for example, in any of the aforementioned positioned.

In one example, an electrosurgical generator coupled to the handle (or within the handle) may generate energy in various modes, for example, radio frequency energy in a cutting mode, a coagulation mode, etc., in order for the end effectors to deliver these different modes of energy to the tissue. In one aspect, the electrosurgical generator and/or the handle may include one or more knobs, dials, buttons, etc. in order to select the energy mode. Additionally, in one example, a fluid source (e.g., a saline source) coupled to the medical device may provide fluid (e.g., saline) to be delivered through the end effectors to the tissue and/or the treatment site. The fluid may be delivered at a constant rate, a pulsed rate, a user-controlled rate, etc. In these aspects, one or more of the energy delivery and/or the fluid delivery may be controlled by one or more actuators (e.g., triggers, buttons, touch screens, foot pedals, etc.).

Some of the medical devices and methods discussed above allow a user to treat tissue by delivering electrical energy to the tissue, and delivering fluid, either simultaneously or sequentially. For example, a user may deliver one of the end effectors to the treatment site, and selectively position the end effector such that one or more portions of the end effector are exposed and configured to deliver energy to the treatment site. Different portions of the end effectors (e.g., the electrode and the loop portion) may be configured to treat the treatment site in different ways as well (e.g., cutting with the electrode, and resection with the loop portion). Moreover, various aspects of the end effectors (e.g., the netting and the wires in FIGS. 5 and 6) may be configured to help retain tissue or material removed from the treatment site.

The user may also deliver fluid distally out of the distal end of the end effectors (e.g., through the electrode), either simultaneously or sequentially with the energy delivered, which may help the user to more quickly and efficiently deliver the medical therapy, for example, cut, dissect, ablate, mark, coagulate, cauterize, or otherwise treat tissue. Moreover, the user may deliver fluid and energy without removing the medical device from the patient or subject, which may help to reduce the costs and duration of the procedure, also potentially reducing the risks to the subject.

While principles of the disclosure are described herein with reference to illustrative aspects for particular applications, it should be understood that the disclosure is not limited thereto. Those having ordinary skill in the art and access to the teachings provided herein will recognize additional modifications, applications, aspects, and substitution of equivalents all fall within the scope of the aspects described herein. Accordingly, the disclosure is not to be considered as limited by the foregoing description.

We claim:

1. A medical device for delivering energy and/or fluid, the medical device comprising:

a handle including a hub for electrically connecting the medical device to an energy source;

a shaft extending distally from the handle, wherein the shaft includes an outer sheath, an inner sheath, and a control wire;

and an end effector at a distal end of the shaft, wherein the end effector includes a loop portion and an electrode coupled to a distal end of the loop portion; and an end cap, wherein the end cap includes an opening extending longitudinally through a portion of the end cap, wherein a portion of the electrode extends through the opening of the end cap, wherein a proximal end of the loop portion is coupled to a distal end of the control wire such that movement of the control wire controls a position of the end effector relative to the distal end of the shaft, wherein the electrode includes a proximal longitudinal portion, a distal longitudinal portion, and a tapered portion between the proximal longitudinal portion and the distal longitudinal portion, and wherein the tapered portion is configured to engage with a proximal portion of the end cap to advance the end cap distally.

2. The medical device of claim 1, wherein the end cap is formed of rubber, is fixedly coupled to a portion of the electrode, and is movable relative to a distal end of the outer sheath.

3. The medical device of claim 2, further comprising:

a fluid port configured to deliver fluid through at least a portion of the shaft, wherein the electrode includes an electrode lumen fluidly connected to the fluid port, and wherein a distal end of the electrode includes an outlet.

4. The medical device of claim 3, wherein a proximal portion of the electrode includes one or more inlets fluidly connected to the electrode lumen.

5. The medical device of claim 4, wherein the one or more inlets are on a radially outer surface of the proximal longitudinal portion of the electrode.

6. The medical device of claim 3, wherein the fluid port is coupled to one or more of the inner sheath and the outer sheath at a position distal to the handle.

7. The medical device of claim 6, wherein the fluid port is configured to deliver fluid through a cavity between the inner sheath and the outer sheath.

8. The medical device of claim 6, wherein the fluid port is configured to deliver fluid through a lumen within the inner sheath.

9. The medical device of claim 2, wherein the electrode includes a widened distal end.

10. The medical device of claim 1, wherein the loop portion forms an opening, wherein the opening includes a wide portion and a tapered or narrowed portion toward a distal end of the loop portion.

11. The medical device of claim 1, wherein the handle includes main body and a movable body, wherein the movable body is movable within a slot in the main body, and wherein the hub is positioned on a portion of the movable body, and wherein the movable body is coupled to the control wire to deliver energy to the end effector and to control movement of the end effector relative to the shaft.

12. The medical device of claim 11, wherein the main body includes a plurality of contours, and wherein the movable body includes one or more detents that interact with one or more of the plurality of contours to lockably position the movable body relative to the main body.

13. The medical device of claim 1, wherein the end effector includes a netting extending across one or more portions of the loop portion.

14. The medical device of claim 1, wherein the loop portion of the end effector includes a plurality of wires forming a basket.

15. A medical device for delivering energy and/or fluid, the medical device comprising:

a handle including a hub for electrically connecting the medical device to an energy source;

a shaft extending distally from the handle, wherein the shaft includes an outer sheath, an inner sheath, and a control wire;

a fluid port configured to deliver fluid through at least a portion of the shaft;

an end cap, wherein the end cap includes an opening extending longitudinally through a portion of the end cap; and an end effector at a distal end of the shaft, wherein the end effector includes a loop portion and an electrode coupled to a distal end of the loop portion, wherein the electrode includes a proximal longitudinal portion, a distal longitudinal portion, and a tapered portion between the proximal longitudinal portion and the distal longitudinal portion, wherein a portion of the electrode extends through the opening of the end cap, wherein a proximal end of the loop portion is coupled to a distal end of the control wire such that movement of the control wire controls a position of the end effector relative to the distal end of the shaft, and wherein the tapered portion is configured to engage with a proximal portion of the end cap to advance the end cap distally.

16. The medical device of claim 15, further comprising:

a cavity between the inner sheath and the outer sheath, wherein the cavity between the inner sheath and the outer sheath is fluidly connected to the fluid port to deliver fluid through the cavity, wherein the end cap is formed of rubber, is fixedly coupled to a portion of the electrode, and is movable relative to a distal end of the outer sheath.

17. The medical device of claim 16, wherein the handle includes a main body and a movable body, wherein the hub is positioned on a portion of the movable body, and wherein the movable body is coupled to the control wire to deliver energy to the end effector and to control movement of the end effector relative to the shaft, wherein the main body includes a plurality of contours, and wherein the movable body includes one or more detents that interact with one or more of the plurality of contours to lockably position the movable body relative to the main body.

18. A method of treating a treatment site, the method comprising:

delivering a distal end of a shaft of a medical device to the treatment site, wherein the medical device includes a handle, a shaft with a distal end, and an end effector movable relative to the distal end of the shaft, wherein the shaft includes an outer sheath, an inner sheath, and an end cap, wherein the end cap includes an opening extending longitudinally through a portion of the end cap, wherein the end effector includes an electrode and a loop portion, wherein a portion of the electrode extends through the opening of the end cap, wherein the electrode includes a proximal longitudinal portion, a distal longitudinal portion, and a tapered portion between the proximal longitudinal portion and the distal longitudinal portion, wherein the handle includes a movable body and a main body, and wherein movement of the movable body controls a position of the end effector;

delivering energy to the treatment site with the electrode of the end effector;

delivering fluid to the treatment site, wherein delivering fluid includes delivering fluid through a port coupled to one or more of the inner sheath and the outer sheath to deliver fluid distally through a cavity between the inner sheath and the outer sheath such that the fluid flows distally into a distal cavity within the outer sheath and into an electrode lumen via one or more inlets in a proximal portion of the electrode;

extending the end effector distally, wherein extending the end effector distally includes distally advancing the movable body of the handle to urge the end effector distally such that the tapered portion of the electrode engages with a proximal portion of the end cap to advance the end cap distally; and delivering energy to the treatment site with the loop portion of the end effector.

19. The method of claim 18, wherein delivering energy to the treatment site with the electrode is configured to cut tissue, and wherein delivering energy to the treatment site with the loop portion is configured to resect tissue.

20. The medical device of claim 5, wherein a proximal end of the electrode is closed and is fixedly coupled the distal end of the loop portion.

* * * * *